(12) United States Patent
Barnett et al.

(10) Patent No.: US 7,955,677 B2
(45) Date of Patent: Jun. 7, 2011

(54) TWO-SIDED NON-STICK RELEASE FILM

(75) Inventors: Brad L. Barnett, Swanton, VT (US); Martin Fletcher, St. Albans, VT (US); Kenneth J. Miller, II, St. Albans, VT (US)

(73) Assignee: Mylan Technologies, Inc., St. Albans, VT (US)

( * ) Notice: Subject to any disclaimer, the term of this patent is extended or adjusted under 35 U.S.C. 154(b) by 922 days.

(21) Appl. No.: 11/296,604

(22) Filed: Dec. 7, 2005

(65) Prior Publication Data
US 2007/0125483 A1   Jun. 7, 2007

(51) Int. Cl.
*B32B 37/00* (2006.01)

(52) U.S. Cl. ........ 428/40.1; 428/42.2; 428/42.3; 428/43; 428/131; 428/134; 428/136; 428/137; 428/138; 424/445; 424/446; 424/447; 424/448; 424/449; 602/41; 602/42; 602/48; 602/79; 156/152

(58) Field of Classification Search .......... None
See application file for complete search history.

(56) References Cited

U.S. PATENT DOCUMENTS

| | | | |
|---|---|---|---|
| 4,627,429 A | 12/1986 | Tsuk | |
| 4,655,767 A | 4/1987 | Woodard et al. | |
| 4,906,463 A | 3/1990 | Cleary et al. | |
| 5,008,110 A * | 4/1991 | Benecke et al. | 424/448 |
| 5,230,898 A | 7/1993 | Horstmann et al. | |
| 5,616,385 A * | 4/1997 | Rothrum et al. | 428/40.1 |
| 5,656,347 A * | 8/1997 | Tynan, Jr. | 428/40.1 |
| 6,277,401 B1 * | 8/2001 | Bello et al. | 424/449 |
| 6,676,961 B1 * | 1/2004 | Lichter | 424/448 |
| 6,814,976 B1 | 11/2004 | Hille et al. | |
| 6,914,169 B1 | 7/2005 | Oota et al. | |
| 2002/0172712 A1 * | 11/2002 | Drizen et al. | 424/486 |
| 2005/0037059 A1 | 2/2005 | Miller | |
| 2006/0068146 A1 * | 3/2006 | Marks et al. | 428/40.1 |

FOREIGN PATENT DOCUMENTS

| | | |
|---|---|---|
| CA | 2 278 753 A1 | 7/1998 |
| EP | 0 382 129 | 8/1990 |
| WO | WO-90/11065 | 10/1990 |
| WO | WO02092141 A1 * | 11/2002 |

\* cited by examiner

*Primary Examiner* — Jennifer C McNeil
*Assistant Examiner* — Vera Katz
(74) *Attorney, Agent, or Firm* — Lerner, David, Littenberg, Krumholz & Mentlik, LLP

(57) ABSTRACT

Assemblies for the adhesive attachment to the skin or mucosa of a host are disclosed. The assembly or transdermal patch includes an outer backing layer, a first layer of adhesive on the inner surface of the outer backing layer, an inner backing layer, and an intermediate release liner between the first layer of adhesive and the inner backing layer. The intermediate release liner includes a releasable surface on both its inner and outer surfaces.

24 Claims, 6 Drawing Sheets

TWO-SIDED NON-STICK RELEASE FILM

BACKGROUND OF THE INVENTION

The present invention relates in general to an assembly for adhesive attachment to the skin or mucosa of a host. More particularly, the present invention relates to transdermal patches and wound dressings, and to methods for their manufacture. Still more particularly, the present invention relates to improvements in the manufacture of adhesive patches.

The use of various systems for adhesive attachment to the skin or mucosa of a patient or host has become increasingly significant. These assemblies can be in the form of wound dressings for direct adhesive application to the skin, without any active agent therein, or transdermal patches for the transdermal delivery of various active agent or drug systems in connection with such attachment. In connection with the general means for preparing such assemblies, there has been an increase in the need to facilitate the handling of adhesive containing assemblies or patches, and for then maintaining them as separable units. In connection with transdermal patch systems, there have been problems engendered by the use of various drugs in which the drug is employed in admixture with an adhesive-based system for application to the skin, or with a non-adhesive-based system with an outer drug permeable adhesive layer.

Simple monolithic transdermal systems incorporate their active agents, i.e., drugs, directly into a single pressure-sensitive adhesive layer. These systems have the advantage of being thin, elegant, and relatively easy to manufacture, but must compromise between optimizing the adhesive matrix for drug delivery versus its ability to adhere to the skin. In addition, these systems still present challenges in connection with their large volume handling and manufacture.

The known "double-disk" transdermal patch uses a larger auxiliary patch over a smaller active agent delivery patch to improve or ensure adhesion to the skin. The adhesive matrixes of the inner and outer patches can be independently optimized for active agent delivery and adhesion, respectively. When the inner and outer patches are laminated together to form the completed system, their adhesive matrixes come into direct contact and begin to equilibrate. As the systems equilibrate, time-dependent changes occur such as the loss of active agents from the inner patch and the simultaneous accumulation of active agents in the outer patch. This phenomena can alter the performance of the transdermal patch if any of the components in the inner patch, especially those that are needed to achieve or sustain active agent delivery, have appreciable affinity for the outer patch adhesive matrix. Moreover, this effect will become more profound with time until equilibrium is achieved.

One solution in preventing the equilibrium of the two adhesive matrixes is to maintain their physical separation, and not to allow the adhesives to come into direct contact with each other during storage. Following application to the skin, these adhesive matrixes will be in direct contact, but the equilibrium process, typically two-three years, is slow compared to the transdermal delivery process, generally less than or equal to seven days. However, in the double-disk transdermal patch, the circumferential edge of the inner patch containing the active agent is exposed to the overlying outer patch and its adhesive matrix. This structure of the double-disk transdermal patch allows for the circumferential migration of active agent from the inner patch into the adhesive matrix of the outer patch.

A solution to some of these problems is set forth in U.S. Patent Publication No. 2005/0037059, which is owned by the assignee of the present application. This application discloses the use of a physical barrier between the patches during storage so that the migration of active agents is inhibited between the inner and outer patches. In accordance with this disclosure, the inner and outer patches are adhered together in a manner creating an annular flap circumferentially about the outer portion of the inner patch and a disposable release liner is interposed between the annular flap and the adhesive material of the outer patch. The outer flap, which contains the active agent, is thus said to be isolated from the underlying portion of the outer portion by the release liner which is releasably attached to the adhesive on the outer patch. This product has proven to be quite successful, but a desire still exists for a more efficient product for completely segregating the annular flap containing the active agent from the underlying portion of the outer patch.

SUMMARY OF THE INVENTION

In accordance with the present invention, these and other objects have now been realized by the discovery of an assembly for adhesive attachment to the skin or mucosa of a host, the assembly comprising an outer backing layer including an inner surface and an outer surface, a first layer of adhesive disposed on the inner surface of the outer backing layer, an inner backing layer, and an intermediate release liner disposed between the first layer of adhesive and the inner backing layer, the intermediate release liner including an inner surface and an outer surface, both the inner surface and the outer surface of the intermediate release liner including a releasable surface. Preferably, the intermediate release liner includes at least one open area and the first adhesive layer includes a portion adhered to the inner backing layer at the at least one open area.

In accordance with one embodiment of the assembly of the present invention, the intermediate release liner comprises a single sheet having the releasable surfaces disposed on both sides of the single sheet.

In accordance with another embodiment of the assembly of the present invention, the intermediate release liner comprises a laminate including at least a pair of sheets affixed to each other, each of the pair of sheets including an inner surface and an outer surface, each inner surface of the pair of sheets being juxtaposed with each other and each of the outer surfaces of the pair of sheets including the releasable surface.

In accordance with another embodiment of the assembly of the present invention, the intermediate release liner comprises an active agent impermeable material. Preferably, the intermediate release layer is releasably adhered to both the first layer of adhesive and the inner backing layer.

In accordance with another embodiment of the assembly of the present invention, the first adhesive layer comprises pressure-sensitive adhesive material for adhering the assembly to the skin or mucosa of the host.

In accordance with another embodiment of the assembly of the present invention, at least one of the pair of sheets comprises a transparent sheet. Preferably, the other of the pair of sheets comprises an opaque sheet. In a preferred embodiment, the assembly includes printed material on the inner surface of the other of the pair of sheets.

In accordance with the present invention, a system has been discovered for the handling of a plurality of adhesive-coated elements, the system comprising a first adhesive-coated material including an outer backing layer having an inner surface and an outer surface and a first layer of adhesive disposed on the inner surface of the outer backing layer, a second adhesive-coated element including an inner surface and an outer surface, the inner surface of the second adhesive-coated element including an inner backing layer, and an intermediate release liner disposed between the first layer of adhesive and the inner backing layer of the second adhesive-coated element, the intermediate release liner including an inner surface and an outer surface, both the inner surface and the outer surface of the intermediate release liner including a releasable surface. In a preferred embodiment, the intermediate release liner comprises a single sheet having the releasable surface disposed on both sides of the single sheet.

In accordance with one embodiment of the system of the present invention, the intermediate release liner comprises a laminate including at least a pair of sheets affixed to each other, each of the pair of sheets including an inner surface and an outer surface, the inner surfaces of the pair of sheets being juxtaposed with each other and each of the outer surfaces of the pair of sheets including the releasable surface.

In accordance with another embodiment of the system or the present invention, the first and second adhesive-coated elements are adapted to include an active agent for release to the skin or mucosa of a host.

In accordance with another embodiment of the system of the present invention, the intermediate release liner comprises an active agent impermeable material.

In accordance with another embodiment of the system of the present invention, the intermediate release liner is releasably adhered to both the first layer of adhesive and the inner backing layer of the second adhesive-coated element.

In accordance with another embodiment of the system of the present invention, the first adhesive layer comprises pressure-sensitive adhesive material.

In accordance with another embodiment of the system of the present invention, the releasable surface of the inner surface of the intermediate release liner has a first release force, and the releasable surface of the outer surface of the intermediate release liner has a second release force, and the first and second release forces are different from each other.

The assembly of the present invention thus not only permits the handling of multiple layered systems, but also inhibits migration of active agents between inner and outer patches by maintaining a physical barrier between the patches during storage. Indeed, it prevent adhesive exposed at the edge of the smaller adhesive system from adhering to the release film of the larger system, and thus accomplishes this result in a more efficient manner than has been known in the past. In applying the assembly or device of the present invention to the handling of stacked adhesive units, it is clear that the assemblies are not limited to transdermal patches or indeed to any systems in which active agents are being employed to the skin or mucosa of a host. Thus, the present system is able to broadly inhibit migration of any component of the assembly, including both active and non-active agents and other ingredients but also including non-active excipients, penetration enhancers, plasticizers, and the like, between the inner and outer layers of adhesive-containing assemblies such as patches.

More specifically, in one embodiment, the assembly or device of the present invention is in the nature of a double-disk system which includes an active agent containing inner patch permanently attached to an adhesive outer patch through an opening provided in a release liner for the outer patch. The inner patch includes an active agent impermeable backing layer, active agent layer containing the active agent to be delivered to the skin or mucosa of a host, which may also be an adhesive matrix layer and a disposable release liner. The outer patch includes a backing layer, adhesive matrix layer which may contain additional active agents, and a disposable release liner preferably of active agent impermeable material, and which includes a releasable surface on both its inner and outer surfaces. The opening in the release liner of the outer patch exposes a portion of the outer patch adhesive matrix. The opening is smaller in size than the active agent inner patch, and provides an anchor point for the inner patch while preventing contact between the inner and outer patches prior to use.

In one embodiment of the present invention there is described a assembly for the release of an active agent to the skin or mucosa of a host, the assembly comprising an outer layer having adhesive properties; an inner layer having an active agent impermeable layer, the inner layer having a portion thereof adhered to the outer layer; and a release liner interposed between a portion of the impermeable layer and a portion of the outer layer, whereupon removal of the release liner exposes the outer layer for adhering the assembly to the skin or mucosa of a host.

In accordance with the present invention, a stacked plurality of components has been devised for the manufacture of an assembly for adhesive attachment to the skin or mucosa of a host, comprising a first plurality of outer backing layers including an inner surface and an outer surface, and a first layer of adhesive disposed on the inner surface of the plurality of outer backing layers, and a second plurality of intermediate release liners including an inner surface and an outer surface, both the inner and outer surfaces of the plurality of intermediate release liners including a releasable surface, whereby the first plurality of outer backing layers and the second plurality of intermediate release liners can be stacked together without adhering to each other. In a preferred embodiment, the intermediate release liner comprises a single sheet having the releasable surfaces disposed on both sides of the single sheet.

In accordance with one embodiment of the stacked plurality of components of the present invention, the intermediate release liner comprises a laminate including at least a pair of sheets affixed to each other, each of the pair of sheets including an inner surface and an outer surface, the inner surfaces of the pair of sheets being juxtaposed with each other and each of the outer surfaces of the pair of sheets including the releasable surface.

In accordance with another embodiment of the stacked plurality of components of the present invention, the first adhesive layer comprises pressure-sensitive adhesive material for adhering the assembly to the skin or mucosa of the host. In a preferred embodiment, at least one of the pair of sheets comprises a transparent sheet. Preferably, the other of the pair of sheets comprises an opaque sheet. In a preferred embodiment, the assembly includes printed material on the inner surface of the other of the pair of sheets.

In accordance with the present invention, a method has also been discovered for producing an adhesive layer for use in the manufacture of an assembly for attachment to the skin or mucosa of a host, the method comprising coating an adhesive layer onto a release liner having a first surface and a second surface, both of the first and second surfaces including a releasable surface, laminating a backing layer onto the first surface of the release liner, temporarily removing the release liner from the adhesive layer, die cutting the release liner, and rejoining the release liner to the adhesive layer. Preferably, the die cutting step comprises slitting the release liner into a plurality of release liner portions. In a preferred embodiment, the die cutting includes punching an opening in the release liner.

In accordance with one embodiment of the method of the present invention, the method includes drying the coated release liner.

In accordance with another embodiment of the method of the present invention, the method includes removing waste from the adhesive layer.

In accordance with another embodiment of the method of the present invention, the method includes winding the rejoined release liner and the backing layer onto a roll.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof may best be understood by reference to the following detailed description when read with the accompanying drawings in which:

DETAILED DESCRIPTION

Figure 1:
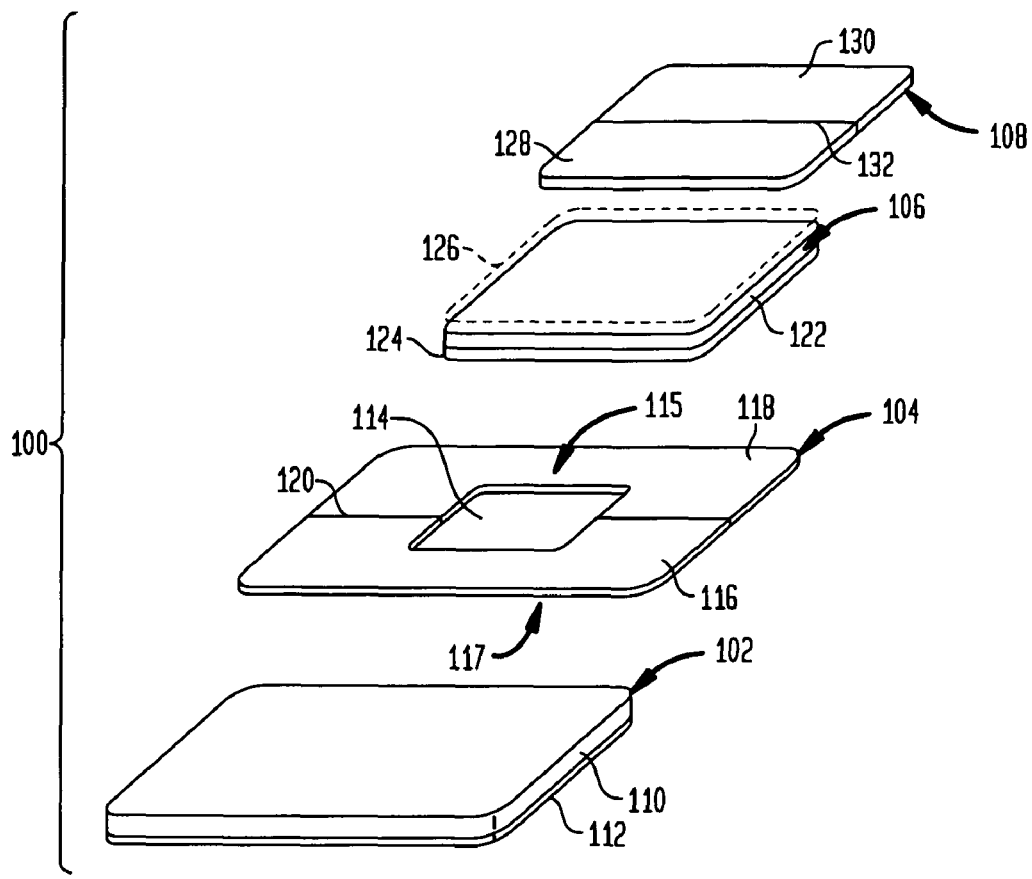
FIG. 1 is a perspective unassembled exploded view of the components of an assembly for the release of an active agent for application to the skin or mucosa of a host in accordance with one embodiment of the present invention.

In describing the preferred embodiments of the invention illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose.

Referring now to the drawings, wherein like reference numerals represent like elements, there is shown in FIG. 1 the unassembled components of an assembly for the administration of one or more active agents to the skin or mucosa of a host in accordance with one embodiment of the present invention. The assembly 100 generally includes an outer patch 102, an outer patch release layer 104, an inner patch 106 and an inner patch release layer 108. The outer and inner patches 102, 106 and release layers 104, 108, which are typically planar layers, are assembled to one another to form a laminate composite structure in the nature of a double disk assembly as to be described hereinafter.

The outer patch 102 includes a flexible adhesive layer 110 and a co-extensive protective backing layer 112 adhered thereto. The adhesive layer 110 provides the primary adhesion of the assembly 100 to the skin or mucosa of a host. Preferably, the adhesive layer 110 is a pressure-sensitive adhesive suitable for contact with the skin or mucosa of a host, e.g., dermatologically acceptable. Optionally, the adhesive layer may be admixed with an active agent or other drug to be administered to a host. In that case, the adhesive layer 110 will be formed from active agent permeable material to allow administration of the active agent.

The backing layer 112 is preferably a thin sheet which is co-extensive with the bottom surface of the adhesive layer 110. Because of the area of skin to which the assembly 100 is to be attached, the backing layer 112 may be flesh-colored for cosmetic reasons and/or bear identifying marks. The backing layer 112 normally provides support and a protective covering for the assembly 100. The backing layer 112 may be formed from a sheet of active agent impermeable or permeable material. Preferably, the backing layer 112 will be formed from active agent impermeable material when an active agent is present in the adhesive layer 110.

The outer patch release layer 104 covers the top surface of the adhesive layer 110 prior to use of the assembly 100 to both protect the adhesive layer from inactivation by ambient dust or other contaminants and to provide an active agent migration barrier as to be described, both with respect to the adhesive layer 110 and with respect to the flexible active agent layer 122 and/or the adhesive layer 126 of the inner patch 106. The release layer 104 has a sufficient surface area and shape to extend at least to the peripheral edges of the adhesive layer 110. An opening 114 within the release layer 104 exposes a portion of the top surface of the adhesive layer 110 of the underlying outer patch 102. The release layer 104 may be formed as a single sheet of material, or multiple sections 116, 118 which are separated by one or more slits 120. Preferably, the release layer 104 is formed from a sheet of active agent impermeable material thereby providing a migration barrier with respect to the active agents in both the inner patch 106 and the outer patch 102.

The inner patch 106 includes a flexible active agent layer 122 and a co-extensive active agent impermeable backing layer 124 adhered to the bottom surface thereof. The active agent layer 122 may be formed from a thermoplastic polymeric matrix which is admixed with the active agent or drug components, and optionally, an active agent enhancer. The polymeric matrix for the active agent layer 122 preferably has pressure-sensitive adhesive properties, or in the alternative, the active agent layer may be coated with an active agent permeable adhesive layer 126 as shown in phantom.

The inner patch release layer 108 may be formed as a similar sheet as release layer 104 from one or more sections 128, 130 separated by a slit 132. The release layer 108 has a surface area and shape to at least extend to the perimeter of the top surface of the active agent layer 122. The release layer 108 covers the top surface of the active agent layer 122 prior to use of the assembly 100 to prevent the release of the active agent. When the active agent layer 122 has pressure-sensitive adhesive properties, or is covered with an active agent permeable adhesive layer, the release layer 108 provides protection from inactivation by ambient dust or other contaminants.

Figure 2:
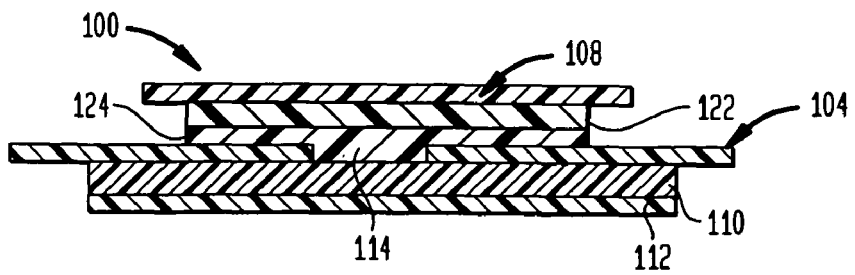
FIG. 2 is an assembled cross-sectional view of the assembly shown in FIG. 1.
Figure 3:
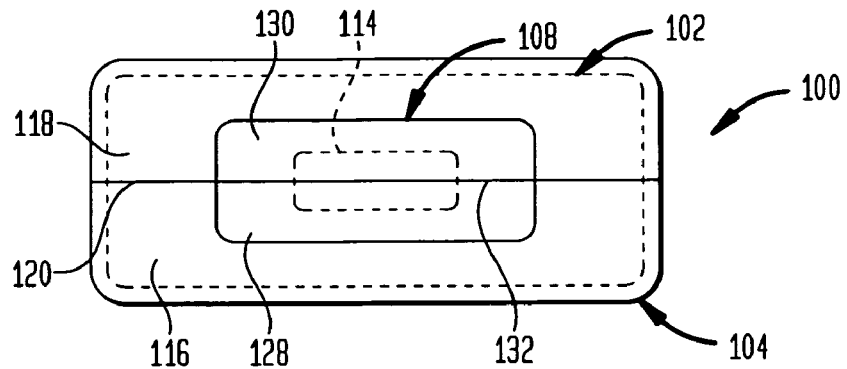
FIG. 3 is a top plan view of the assembly shown in FIG. 1.

The assembly 100 is shown in assembled relationship in FIGS. 2 and 3 in the nature of a laminate composite assembly of generally planar layers. The release liner 104 includes releasable surfaces 115 and 117, respectively, and is thus releasably adhered in co-extensive contact with the top surface of adhesive layer 110 of the outer patch 102, and to the outer surface of active agent permeable backing layer 124, and thus also with respect to any active agent and/or adhesive, and/or any other ingredient of the active agent layer 122 and/or adhesive layer 126.

In the case where the release liner 104 includes a single sheet of material, release coatings must be applied to both sides of the release liner 104. The release coatings generally employed comprise coatings of silicon, teflon, or other suitable such coatings which are conventional in the preparation of release layers. These can include, for example, fluorocarbon and fluorosilicone coatings which are compatible with silicone-based adhesives.

The opening 114 in release layer 104 exposes a portion of the top surface of the underlying adhesive layer 110. The inner patch 106 is adhered to the outer patch 102 by bonding the impermeable backing layer 124 to the adhesive layer 110 exposed within the opening 114. The surface area of the opening 114 is smaller than the surface area of inner patch 106. This results in the inner patch 106 having an annular portion in the nature of a flap surrounding opening 114, which is not bonded to the adhesive layer 110 as a result of an interposed portion of the release liner 104. Likewise, the peripheral edges of the active agent layer 122 and/or the adhesive layer 126 are separated from the adhesive layer 110 by a portion of the release liner 104. The presence of releasable surface 115 thereon thus also prevents this active agent, adhesive or other material from adhering to the surface of release layer 104. The impermeable backing layer 124 and impermeable release layer 104 therefore not only isolate the active agent layer 122 to inhibit migration of an active agent from the active agent layer to the adhesive layer 110 during storage of the assembly 100 prior to use, but also prevent any adhesive from adhesive layer 126 from migrating from the edge of inner patch 106 to adhere to the prior non-release-coated surface of release liner 104 so as to interfere with removal of the release liner prior to use.

The assembly 100 is prepared for application to the skin or mucosa of a host by removing release layers 104, 108. To facilitate removal of release layer 104, it is preferable that at least a portion of the release layer extend beyond the periphery of the underlying adhesive layer 110. The extended portion may be in the nature of a tab or annular portion circumscribing the entire perimeter or portion of the adhesive layer 110 as shown in FIG. 3. In this manner, each section 116, 118 of the release layer 104 may be removed to expose the top surface of the adhesive layer 110 surrounding the inner patch 106 containing the active agent. The exposed surface portion of the adhesive layer 110 will have sufficient surface area to provide adhesion of the assembly 100 to the skin or mucosa of a host during use. Removal of the sections 116, 118 are undertaken individually as a result of their separation by slit 120. This enables removal of the sections 116, 118 notwithstanding a portion of the sections surrounding the opening 114 being interposed between the adhesive layer 110 and impermeable backing layer 124 of the inner patch 106. Most significantly, the presence of releasable surfaces 115 and 117 on both sides of release liner 104 permits this operation to proceed seamlessly, and without adherence to either side thereof or contact of the user's fingers with either adhesive.

Figure 3A:
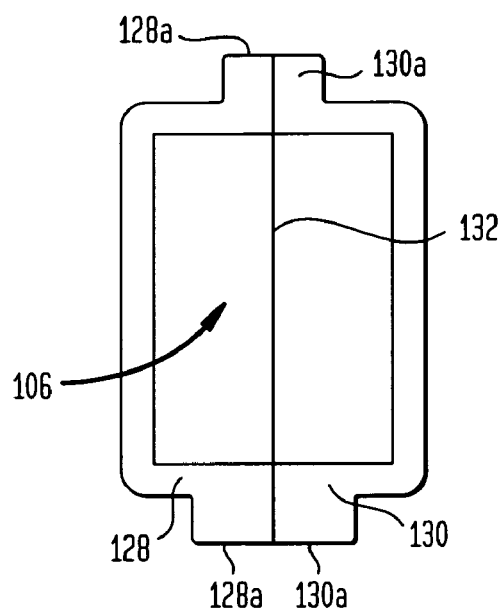
FIG. 3A is a top plan view of another embodiment of a portion of the assembly shown in FIG. 1.
Figure 4:
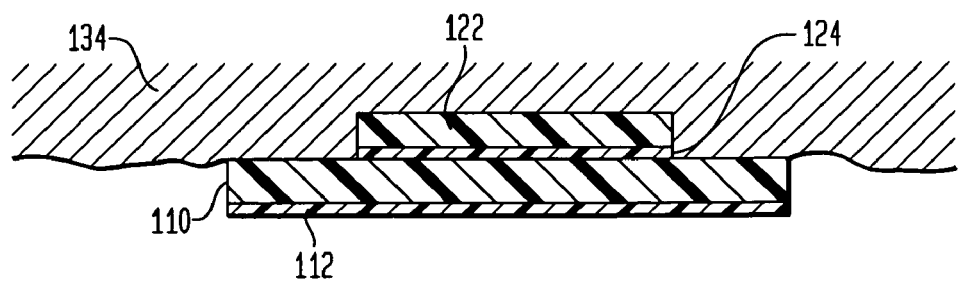
FIG. 4 is a cross-sectional view of the application of the assembly shown in FIG. 2 adhered to the skin or mucosa of a host.

In a like manner, the release layer 108, which in this case requires a releasable surface on only one side thereof, i.e., the side facing adhesive layer 126 and/or active agent layer 122, is removed from the top surface of the active agent layer 122 by grasping an extended portion of sections 128, 130. It is therefore possible, and in some cases desirable, for the individual sections 128 and 130 of release layer 108 to have extended portions which extend beyond the perimeter of the inner patch 106. For example, reference is made to FIG. 3A hereof in which the sections 128 and 130 of the inner patch release layer 108 include an outer circumference which is larger than the circumference of the inner patch 106 and furthermore includes extended tab-like sections 130a and 128a, preferably at both ends of the release layer 108. In this manner, preferably after the outer patch release layer 104 has been removed, the inner patch release layer 108 can be removed by grasping tabs 130a and 128a, to thus remove the portions 128 and 130 thereof. The assembly 100 is adhered to the skin or mucosa of a host 134 as shown in FIG. 4 with the active agent layer 122 in contact with the host. The host to which an active agent is administered by means of the inventive assembly may be any host on which a drug or other active agent has the desired effect. The host may be, for example, a mammal such as a human being, or, for that matter, any warm-blooded or cold-blooded animal. The advantage of administering the active agent may be therapeutic or experimental. The assembly 100 of this invention may also be used for any other advantageous purpose.

The extended sections of the release layer 108 may be as described above with respect to FIG. 3A or as described with respect to release layer 104. However, it is to be understood that it is not required that the release layers 104, 108 extend beyond the periphery of their underlying adhesive layer 110 and active agent layer 122, respectively. The extension of the release layers 104, 108 merely facilitates removal of the release layers by the user prior to application of the assembly 100.

The individual components of the assembly 100 have been illustrated as being rectangular in shape for illustrative purposes only. It is to be understood that the assembly 100 and its components may have any other shape, such as square, round, oval and the like. For example, the outer patch 102 may have a square shape, while the inner patch 106 may be circular. In addition, it is not a requirement of the present invention that opening 114 be rectangular, and may be in the form of a polygon, such as a hexagonal shape for example, or may be formed as a plurality of non-contiguous openings within the release layer 104. The opening 114 serves one function of enabling bonding of the inner patch 106 to the outer patch 102 in assembling the assembly 100. In addition, the surface area of opening 114 in relationship to the surface area of the inner patch 108 defines the extent of the circumferential portion of the inner patch which is separated from the adhesive layer 110 by the interposed release layer 104. Accordingly, the size, shape and location of the opening 114 can be tailored to accommodate the migration of an active agent based upon, for example, the migration rate of the active agent within the active agent layer 122. In addition, the size of the opening 114 can also be employed to effect migration of an active agent between adhesive layers; namely, from adhesive layer 110 through the opening 114 into the active agent layer 122 and/or the adhesive layer 126.

Figure 5:
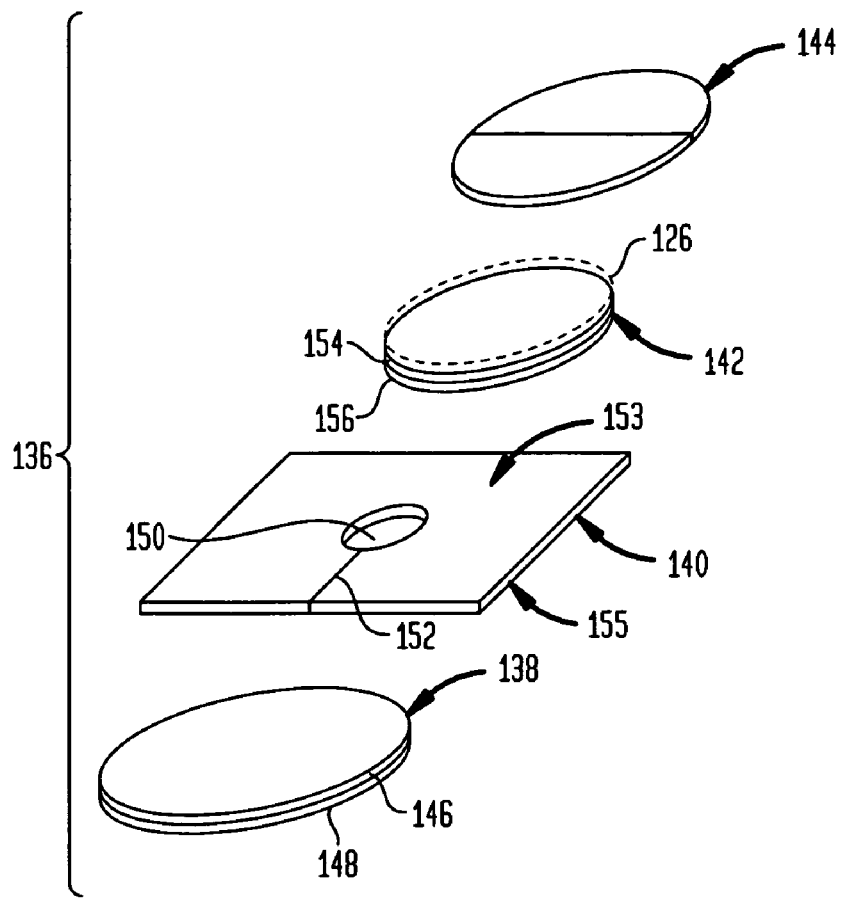
FIG. 5 is a perspective unassembled exploded view of the components of an assembly for the release of an active agent for application to the skin or mucosa of a host in accordance with another embodiment of the present invention.
Figure 6:
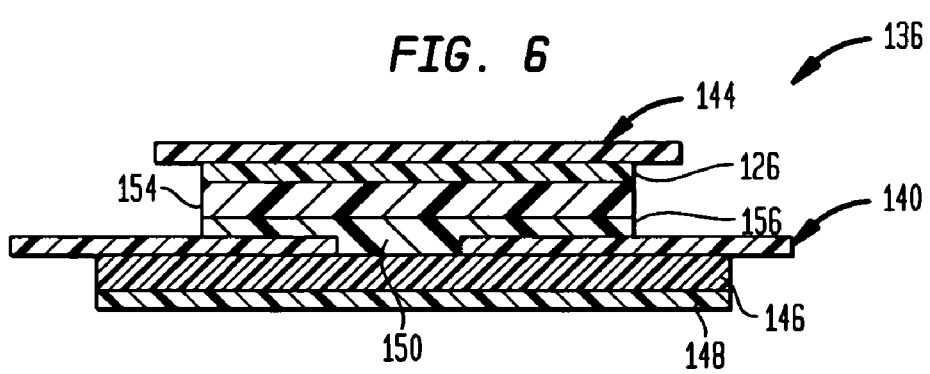
FIG. 6 is an assembled cross-sectional view of the assembly shown in FIG. 5.
Figure 7:
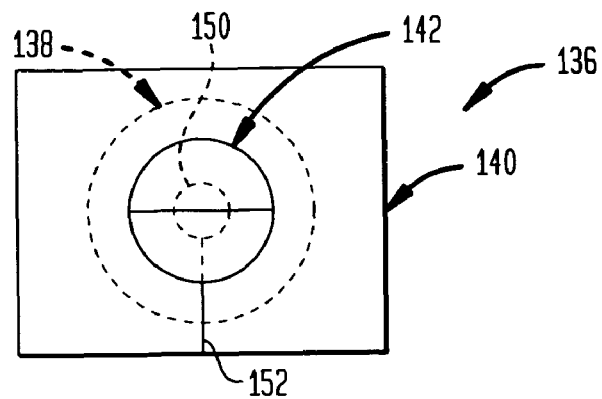
FIG. 7 is a top plan view of the assembly shown in FIG. 6.

Referring to FIGS. 5-7, there is disclosed another embodiment of an assembly 136 adapted for the administration of an active agent to the skin or mucosa of a host. The assembly 136 differs in one aspect from the assembly 100 in the shape of its component parts. In this regard, the assembly 106 includes a circular outer patch 138, a square or rectangular outer patch release layer 140, a circular inner patch 142 and a circular inner patch release layer 144.

The outer patch 138 includes an adhesive layer 146 and a co-extensive outer backing layer 148. The adhesive layer 146 may be in the nature of a pressure-sensitive adhesive, and optionally, admixed with an active agent or other drug to be administered to a host. In this event, the backing layer 148 will be in the nature of a sheet of active agent impermeable material.

The release layer 140, like release layer 104, is preferably formed from a sheet of active agent impermeable material which is releasably adhered to both the top surface of the adhesive layer 146 of the outer patch 138 and to the exposed edge of the active agent layer 154 (or, alternately the adhesive layer 126) of the inner patch 142, by means of having releasable surfaces 153 and 155, respectively, on both sides of the release layer 140. The release layer 140 includes an opening 150 which exposes a portion of the top surface of the adhesive layer 146 through which the inner patch 142 is adhered. Removal of the release layer 140 is facilitated by a slit 152 extending from an outer edge of the release layer to the opening 150.

The inner patch 142 includes an active agent layer 154 which may be a mixture of polymeric materials along with the active agent or other ingredients so as to posses pressure-sensitive adhesive properties for adhering (at least in part) the assembly 136 to the skin or mucosa of a host. That is, the overall ability of the assembly 136 to adhere reliably to the skin or mucosa of the host can depend on both the inner patch 142 and the outer patch 138 and the adhesives thereof. The top surface of the active agent layer 154 can be coated with an active agent permeable adhesive layer 126, but as is the case with the adhesive layer 126 shown and discussed with respect to FIG. 2, the layer can be eliminated, and is optional therein. It is also contemplated, although not shown, that the inner patch 142 may include a rate-controlling polymer layer to provide a means for controlling the rate at which the active agent is released from the surface of the inner patch 142 to the skin or mucosa of the host. The rate-controlling polymer layer may be adhered to the surface of the active agent layer 154 using any suitable active agent permeable adhesive such as that used for active agent layer 154 or adhesive layer 126.

The inner patch 142 further includes an active agent impermeable backing layer 156 adhered to the bottom surface of the active agent layer 154. The impermeable backing layer 156 may be adhered using the pressure-sensitive adhesive properties of the active agent layer 154, or by a layer, not shown, of preferably an active agent impermeable adhesive. The release layer 144, similar to release layer 108, is releasably adhered to the active agent layer 154 or, alternately, the adhesive layer 126 of the inner patch 142 for preventing release of the active agent and for protecting and preventing contamination to the adhesive properties of the inner patch prior to application to the host and initiation of therapy. It can thus be seen that release layer 144 requires only a single releasable surface corresponding to releasable surface 153 or releasable surface 155 on both sides of release layer 140. The opposite side of release layer 144 from that which is in contact with either the active agent layer 154 or the adhesive layer 126 of the inner patch 142 thus does not require a releasable surface since it will not be in contact with any surface from which it needs to be released.

A portion of the release layer 140 is interposed between a portion of the bottom surface of the inner patch 142 and the top surface of the adhesive layer 146 of the outer patch 138. The inner patch 142, release layer 140, and outer patch 138 are aligned and stacked one upon the other so as to form an assembly in which an annular portion of the release layer 140 is interposed between the outer edge of inner patch 142 and the inner edge of release layer opening 150. This annular region separating the outer edge of inner patch 142 and the inner edge of opening 150 isolates active agent layer 154 from adhesive layer 146 to prevent migration of any active agent(s) therebetween. Similarly, the presence of releasable surface 153 in the upper surface of release liner 140 prevents any adhesive from adhesive layer 126, and most particularly from the exposed edges of the adhesive layer 126, for adhesively attaching the inner patch 142 to the surface 153 of the release layer 140. Upon removal of the release layer 140, an annular portion of the top surface of the adhesive layer 146 is exposed surrounding the perimeter of the inner patch 142. The adhesive layer 146 provides sufficient adhesion to adhere the assembly 136 to the skin or mucosa of a host. The adhesion of the assembly 136 may optionally be enhanced by the inner patch 142 having either pressure-sensitive adhesion properties or the incorporation of an active agent permeable adhesive layer 126.

As previously described, the active agent or drug is contained within the active agent layer 122, 154, and optionally in the adhesive layer 110, 146. The active agent may be, for example, systemic or topical drugs. Individual active agents or mixtures thereof, if desired, can be employed. Any drug which passes through the skin or mucosa of a host can be employed for internal administration in the assembly of the invention so long as the drug will pass through the permeable adhesive layer or layers present. The active agent and thermoplastic matrix polymer can be melt-blended in an extruder and then formed into the active agent layer 122, 154 or adhesive layer 110, 146 by extrusion. Other known processes for incorporation of the active agent such as solvent blending are contemplated.

Suitable systemic drugs for administration by the assemblies of the present invention include psychoactive agents such as nicotine, caffeine, mesocarb, mefexamide, cannabinols such as THC, and the like, sedatives such as diazepam, mepiridine, uldazepam, tybamate, metaclazepam, tetrabarbitol and the like, antidepressants such as amitryptyline, imipramine desipramine, nialamide, melitracen, isocarboxazid, and the like, anticonvulsants such as phenobarbitol, carbamazepine, methsuximide, 2-ethyl-2-phenylmalonamide (PEMA), phenyloin and the like, steroids such as progesterone, testosterone, pregnanediol, progestin, estradiol, anabolic steroids and the like, analgesics, including narcotic analgesics such as codeine, morphine, fentanyl, analorphine, demeral and the like, and analgesics such as acetaminophen, aspirin, and the like, antimicrobial agents such as sulconazole, siccanin, silver sulfadiazine, bentiacide, and the like, tranquilizers such as alprazolam, meprobamate and the like, antineoplastic agents such as sulfosfamide, rufocromomycin and the like, and antibiotic agents such as tetracycline, penicillin, streptozcin and the like.

The quantity of active agent present is that quantity sufficient to provide a pharmaceutically or physiologically effective dosage rate of the active agent to a host in need thereof. This quantity can be readily determined by those of ordinary skill in the art without undue experimentation as shown in the examples set forth below.

The assembly 100, 136 of the present invention optionally include a rate-controlling polymer layer. The polymers suitable for use as the rate-controlling polymer layer are conventional in the art and need not be discussed in detail here. Some preferred materials include, for example, polyethylene, polypropylene, ethylene vinyl acetate copolymer (EVA), copolyesters (e.g., HYTREL) and polyurethanes.

The rate of permeation of the active agent through the rate-controlling polymer layer depends on factors such as the affinity of the active agent for the polymer layer, molecular size of the active agent, polymeric structure of the carrier layer and the thickness of the layer. Therefore, the appropriate rate-controlling polymeric material and its thickness depend on the active agent used and the desired rate of permeation. The selection of a polymer layer and its thickness provides a means, if desired, for controlling the dosage rate to the skin or mucosa.

Further, an enhancer to promote the penetration of the active agent through the skin may be included in either the active agent layers 122, 154, rate-controlling polymer layers or the active agent permeable adhesive layers, if present. The enhancer may be incorporated into these layers by solvent blending or, more preferably, by melt-blending by the same process utilized to incorporate the active agent into either the active agent layers 122, 154 or the adhesive layers 110, 146, which adhesive layers may also include an enhancer.

Suitable enhancers include those described in U.S. Pat. No. 4,573,996, such as the following enhancers: monovalent, saturated and unsaturated aliphatic and cycloaliphatic alcohols having 6 to 12 carbon atoms such as cyclohexanol, lauryl alcohol and the like; aliphatic and cycloaliphatic hydrocarbons such as mineral oils; cycloaliphatic and aromatic aldehydes and ketones such as cyclohexanone; N,N-di (lower alkyl) acetamides such as N,N-diethyl acetamide, N,N-dimethyl acetamide, N-(2-hydroxyethyl) acetamide, and the like; aliphatic and cycloaliphatic esters such as isopropyl myristate and lauricidin; N,N-di (lower alkyl) sulfoxides such as decylmethyl sulfoxide; essential oils; nitrated aliphatic and cycloaliphatic hydrocarbons such as N-methyl-2-Pyrrolidone, Azone; salicylates, polyalkylene glycol silicates; aliphatic acids such as oleic acid and lauric acid, terpenes such as cineole, surfactants such as sodium lauryl sulfate, siloxanes such as hexamethyl siloxane; mixtures of the above materials; and the like.

The backing layer 124, 156 is preferably made of a material or combination of materials that is substantially impermeable to the layer or layers with which it can be in, contact, e.g., to the active agent layers 122, 154, the adhesive layer 110, 146 and the active agents or ingredients contained therein, the adhesives, etc. In this regard, a primary objective is to prevent migration or seepage of the active agents or ingredients through the backing layer 124, 156 of the inner patch 106, 142 into the underlying adhesive layer 110, 146. The backing layer 112, 148 may also be made from a similar material being impermeable to the active agents, particularly when the active agents are present also within the adhesive layer 110, 146. The backing layer 112, 148 is not required to be impermeable to the active agents, particularly when there are no active agents in the adhesive layer 110, 146. Thus, it is not necessary in all instances that the backing layer 112, 148 be impermeable to the active agents.

By impermeable, it is meant that the other components in contact with the backing layer or component under consideration will not appreciably permeate through such layer or component for the normal period of use and storage of the assembly. Some suitable materials for the backing layer include, for example, cellophane, cellulose acetate, ethyl cellulose, plasticized vinyl acetate-vinyl chloride copolymers, ethylene-vinyl acetate copolymer, polyethylene terephthalate, polyvinyl chloride, nylon, polyethylene, polypropylene and polyvinylidene chloride (e.g., SARAN), or combinations/laminates thereof.

The assembly 100, 136 includes a release liner attached to the assembly such as at the surfaces to be adhered to the skin or mucosa of a host. The release liner may be made of the same materials suitable for use in the backing layer provided they are active agent impermeable. Most significantly, the release liner 104, 140 must include releasable surfaces on both faces thereof. These release liners are thus made removable or releasable from the adhesive layers or active agent layers by, for example, conventional treatment with silicon, Teflon or other suitable coating on the surface thereof. The application of such coatings on both surfaces of these release liners 104, 140 thus not only accomplishes the purpose of ready release from the surface of the adhesive layers 110, 146 on the outer patches, but they also permit release from any adhesive or other such materials present on the inner patches 106, 142, such as will be present along the outer edges or surfaces thereof. The removal of the assembly 100, 136 from the release liner may also be provided by mechanical treatment of the protective layer, e.g., by embossing the protective liner.

While the release liners between the inner and outer patches used in the present invention must include releasable surfaces on both faces thereof, this can be accomplished in a number of ways. As is discussed above, in the embodiment in which a single sheet of material is employed, a release coating is applied to both surfaces of that sheet. The release coating can be applied to a single sheet, or a conventional release liner having releasable surfaces on one surface thereof can be modified to include a second release surface on the opposite side thereof. In the alternative, however, the release liners 104, 140 of the present invention can be produced from a laminate of two or more sheets. In the embodiment in which, for example, two sheets are used, two separate conventional one-sided release liner films can be attached together, thus producing a laminated sheet with release coatings on either surface. In addition two uncoated sheets can be attached together and then releasable surfaces produced on both outer surfaces thereof after such attachment. All of the above provides additional flexibility to the manufacturer which can apply various commercially available release films or custom manufactured release films to one or both of the surfaces simultaneously, in separate operations, or the like.

In the case of either a single or multiple sheet release liner 104, 140, in one preferred embodiment of this invention it is possible to have either the same or dissimilar release coatings applied to the two sides of the liner itself. It is thus possible to selectively alter the release characteristics of one or both sides of the release liner for particular purposes. For example, when laminating a coated adhesive to itself, it would be possible to predict which bond has a lighter or heavier release force for removal therefrom. In this manner, one could, for example, isolate a dried film or apply a dried film to a new substrate when constructing a multilayer laminate from dissimilar materials or building up multiple layers of a common adhesive. Therefore, in quantifying particular release forces or differentiating between the release forces on the two sides of release liner 104, 140, one could conventionally utilize a standard adhesive tape and devise a standard measurement based on the force required to peel that tape from the release liner. On the other hand, the required peel force to separate the layers of the finished product could be directly quantified and tabulated if that were desirable.

In one particular embodiment of the present invention, in which a laminated construction is employed, one layer in the laminate could be a commercially available single-sided release film, which has a clear configuration. This is, in turn, attached to a second laminate which is also possibly a commercially available film (with or without a release coating), but in which case it is a colored or opaque release film. In one particular embodiment, for example, the second or opaque release film may be printed on the non-release surface thereof (before or after the application of a release agent if necessary). In this manner, the resultant product is a printed two-sided release film in which the printing is visible through the release coating on the first clear single-sided release film discussed above.

Examples of suitable pressure-sensitive-adhesive materials for use in the present invention as an active agent impermeable adhesive include some natural rubber and synthetic rubber adhesives and cross-linkable laminating adhesives. Examples of suitable natural rubber adhesives include R-1072 from B.F. Goodrich Co., No. 735 from C.L. Hathaway, and No. 5702 from Evans St. Clair. Examples of synthetic rubber adhesives include Jowatherem 270-00 and Jowatherem S-3202 from Jowat Corp. and 70-9416 from National Starch. Other suitable laminating adhesives include the Dow Corning laminating silicone adhesives and the Lord Corporation Tycel 7900 series laminating adhesives. Also contemplated are acrylic copolymers such as those available from National Starch and Chemical Co. of Bridgewater, N.J. under the marks DURO-TAK 87-2516 and DURO-TAK 87-2287. The adhesives most impermeable to most active ingredients are cross-linkable laminating adhesives, which are well-known to those of ordinary skill in the art.

The active agent permeable adhesive layers are preferably a pressure-sensitive adhesive. Any of the well-known, dermatologically acceptable, pressure-sensitive adhesives which permit drug migration therethrough can be used in the present invention. Some suitable permeable adhesives include acrylic or methacrylic resins such as polymers of alcohol esters of acrylic or methacrylic acids and alcohols such as n-butanol, isopentanol, 2-methylbutanol, 1-methyl-butanol, 1-methylpentanol, 2-methylpentanol, 3-methylpentanol, 2-ethyl-butanol, isooctanol, n-decanol, or n-dodecanol, alone or copolymerized with ethylenically unsaturated monomers such as acrylic acid, methacrylic acid, acrylamide, methacrylamides, N-alkoxymethyl acrylamides, N-alkoxymethyl methacrylamides, N-t-butyl-acrylamide, itaconic acid, vinyl acetate, N-branched alkyl maleamic acids wherein the alkyl group has 10-24 carbon atoms, glycol diacrylates, or mixtures of these monomers; polyurethane elastomers; vinyl polymers such as polyvinyl alcohol, polyvinyl ethers, polyvinyl pyrrolidone, and polyvinyl acetate; urea formaldehyde resins; phenol formaldehyde resins, resorcinol formaldehyde resins; cellulose derivatives such as ethylcellulose, methylcellulose, nitrocellulose, cellulose acetate butyrate and carboxymethylcellulose; and natural gums such as guar, acacia, pectina, starch, destria, gelatin, casein, etc.

Other suitable pressure-sensitive adhesives include polyisobutylene pressure-sensitive adhesives, rubber pressure-sensitive adhesives and silicone pressure-sensitive adhesives. The adhesives may also be compounded with tackifiers and stabilizers as is well-known in the art.

Adhesives that are preferred for their active agent permeability include acrylic copolymer adhesives such as Avery Chemical Company's AS-351 HSX, preferably at a coating weight of between 75 and 125 g/m². This pressure-sensitive adhesive is a cross-linkable polymer which provides a permanently tacky film.

Other such adhesives that can also be used for these purposes include an acrylic pressure-sensitive adhesive sold by National Starch and Chemical Co. under the designation DURO-TAK 80-1054. This adhesive has a solids content of 47.5%, a viscosity of 3,000 cps., and plasticity (Williams) of 2.9 mm. It is generally used with a solvent system including ethyl acetate, heptane, isopropyl alcohol and toluene. Another such adhesive is sold by the UCB Group under the designation GELVA Multipolymer Emulsion 2484, and comprises a stable aqueous acrylic emulsion pressure-sensitive adhesive having a solids content of 59% and a viscosity of 1,500 to 2,300 cps. Examples of other acrylic adhesives include Gelva 788 and 733 from UCB, PS-41 from C.L.-Hathaway, Vr-0833 from H. B. Fuller, Adcot 73A207A from Morton Chemical, Nos. 80-2404, 80-1054, 72-9056 and 72-9399 from National Starch, Nos. E-2015, E-2067 and E-1960 from Rohm & Haas, M-6112 from Uniroyal, Inc. and Daratak 74 L from W.R. Grace. Suitable rubber adhesives include Duro-Tak 36-6172 from National Starch and Morstik 118 from Morton Chemical. An example of a suitable silicone adhesive is 7-4502 from Dow Corning.

The width (i.e., surface area) and thickness of the permeable adhesive layer for contact with the skin or mucosa is that width and thickness which provides sufficient permeability to the active agent or active agent enhancer, adequately adhere to the skin or mucosa, and provide a suitable surface area to allow the dosage rate desired to the skin or mucosa. These widths and thicknesses are conventional in the art and therefore need not be discussed in detail here.

The active agent layers 122, 154 are preferably monolithic polymeric active agent carrier layers. Thus, in essence, these monolithic active agent carrier layers are admixed by means of melt-blending with the active agent or drug component or active agent enhancer, or both, and basically comprise a thermoplastic polymeric matrix. However, monolithic polymer matrix carrier layers which blend the active agent with a matrix polymer in a common solvent and then evaporate the solvent to form a plastic film are contemplated. As is readily understood by those of ordinary skill in the art, the step of melt-blending requires the use of a thermoplastic polymer, that is, one that softens and melts when exposed to heat and then returns to its original condition when cooled. Suitable thermoplastic matrix polymers are the thermoplastic polyurethanes, including the polyether polyurethanes. These include such commercial polyurethane compositions such as Dow Chemical Company's PELLETHANE, including its 2363-80 AE grade thereof; K.J. Quin's Q-THANE; B.F. Goodrich's ESTANE; Mobay Chemical Company's TXIN; and others.

Suitable thermoplastic matrix polymers also include various polyesters, such as the copolymers of various cyclic polyesters including DuPont's HYTREL, including its 4056 grade thereof, and General Electric's LOMOD both of which are copolymers of polyether prepolymers and polybutylene terephthalate and polyisobutylene terephthalate, respectively, as well as Eastman Chemical's PCCE. Other suitable polymers include ethylene methacrylic and acrylic acid copolymers. For example, ethylene methacrylic acid having the commercial designation NUCREL 699 is particularly suitable as a thermoplastic matrix polymer.

The various layers of the assembly 100, 136 of the present invention may be combined to form a laminate by methods conventional in the art. One such process includes combining the active agent and a thermoplastic matrix polymer by melt-blending the two components forming the polymer layers by extrusion. Another known process is referred to as a solvent-blend process using solvated components which form an admixture that is coated onto a substrate such as a release liner and subsequently dried. The melt-blending process is described in further detail in U.S. Pat. No. 6,010,715, the disclosure of which is incorporated herein by reference.

There are also known various materials for use in the construction of the assembly 100, 136 of the present invention for the backing layers, release layers, adhesive layers, active agent layers, pressure-sensitive adhesive layers, active agent permeable adhesive layers, active agent impermeable adhesive layers, active agent impermeable layers, active agent permeable adhesive layers, etc. Suitable materials are disclosed in U.S. Pat. Nos. 5,064,422, 5,123,900, 5,503,844 and 5,948,433, the disclosures of which are incorporated herein by reference.

Figure 8:
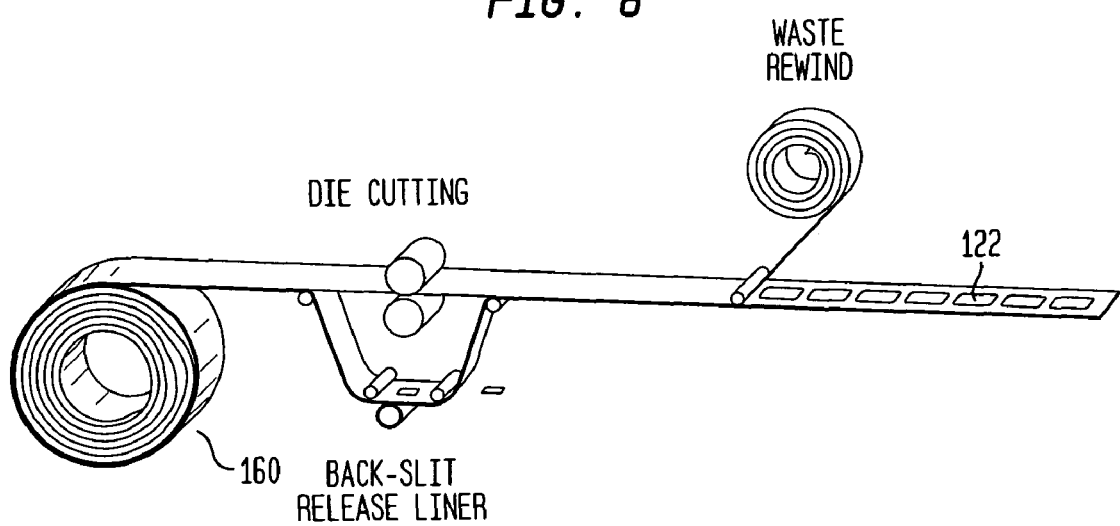
FIGS. 8-10 are diagrammatic illustrations of one embodiment a method of forming assemblies in accordance with the present invention.
Figure 9:
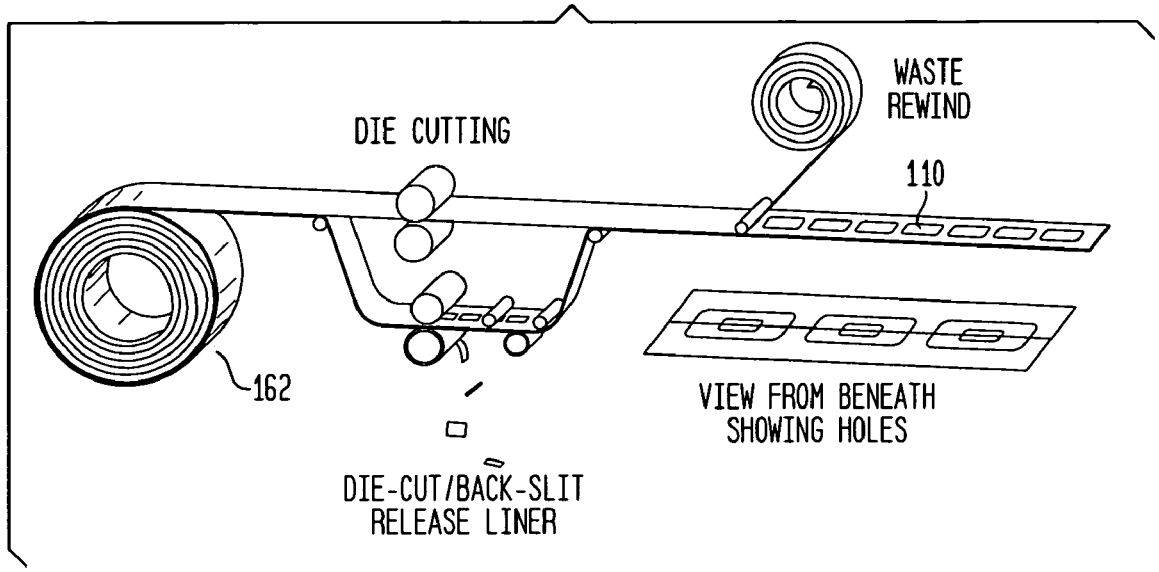
Figure 10:
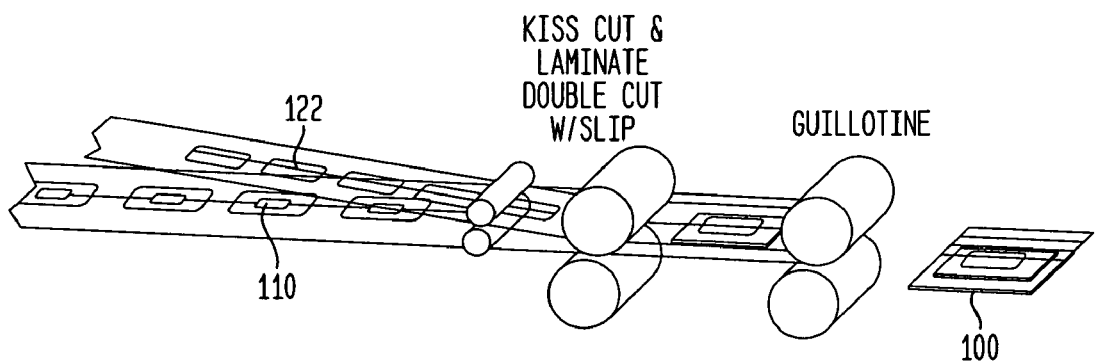

Referring to FIGS. 8-10, there is illustrated one example of a method of manufacturing the assembly 100, 136 via a solvent-blending process. With reference to the assembly 100, the active agent layer 122 is formed by admixing solvated polymer materials such as those having pressure-sensitive adhesive properties in conjunction with the active agent to be administered to the skin or mucosa of a host. The active agent polymeric admixture is coated onto a release liner, dried, laminated with an active agent impermeable backing layer, and wound into a continuous supply roll 160. The release liner is separated from the active agent layer and back slit to form slit 132 while the active agent layer is die cut to the desired size and shape of the inner patch 106. The release liner and active agent layer are re-joined, followed by removal of the extraneous active agent layer.

In a similar solvent-blending process as shown in FIG. 9, the pressure-sensitive adhesive matrix materials forming the adhesive layer 110 are coated onto a release liner which has release characteristics on both sides thereof, dried, laminated with a backing layer, and wound to form a supply roll 162. The release liner is removed from the adhesive layer, die cut to form opening 114 and back slit to form slit 120. The release liner is re-joined with the adhesive layer, followed by the removal of the waste adhesive layer.

Referring to FIG. 10, the supported active agent layer 122 is aligned overlying and in registration with the supported adhesive layer 110, and adhered thereto through the opening in the release liner in a continuous process. The release liner for the active agent layer is cut to appropriate size and shape, followed by a guillotine process for severing the outer patch release layer to form the completed assembly 100.

It is to be understood that the above description of a method of making the assembly 100, 136, as described with reference to FIGS. 8-10, is by way of one illustrative example only. In this regard, it is contemplated that other methods for manufacturing the assembly 100, 136 are contemplated, and accordingly, the described method is not to be interpreted as any limitation upon the scope of the present invention.

Figure 11:
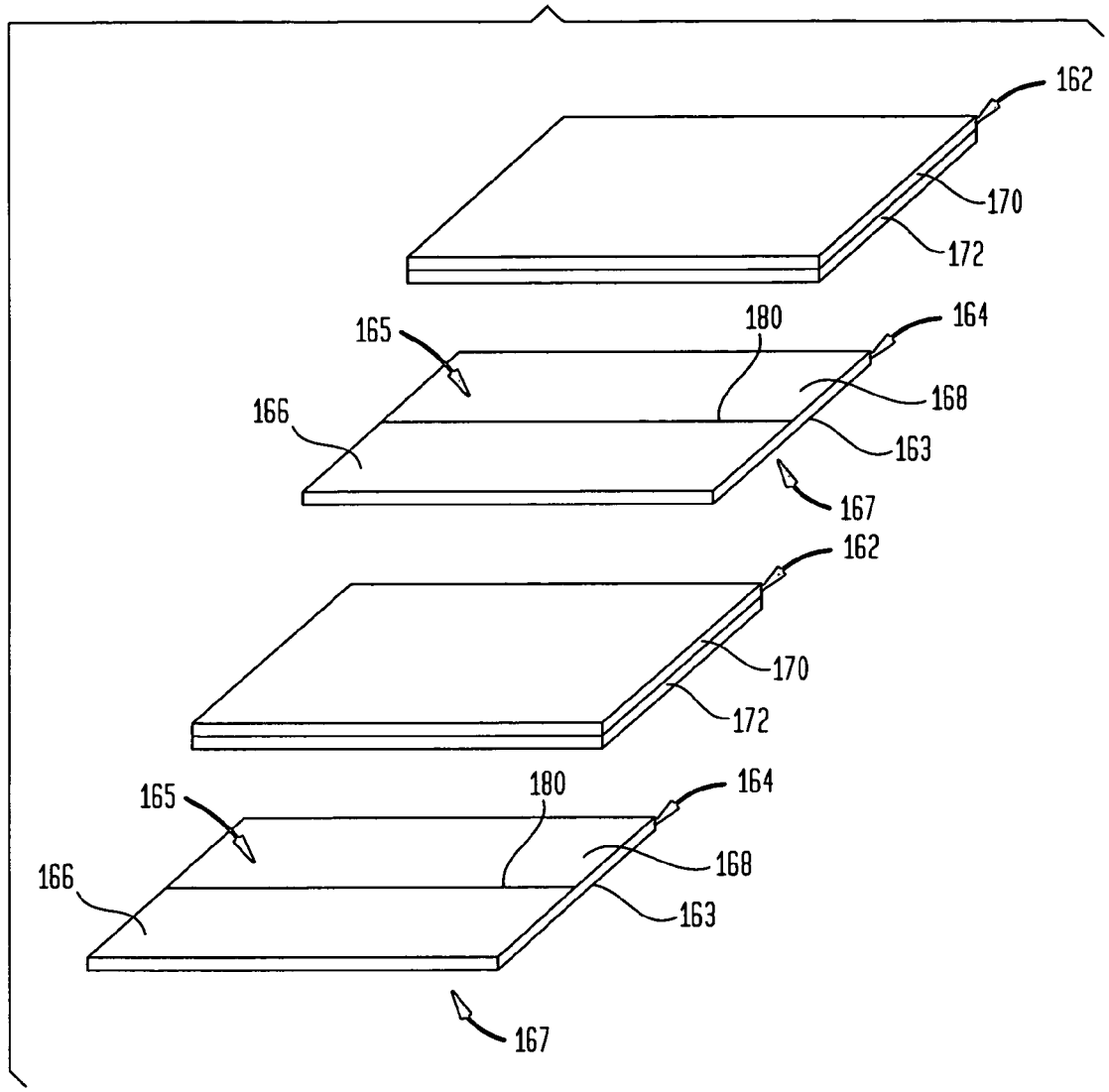
FIG. 11 is a perspective unassembled exploded view of the components for a system to manufacture a multiplicity of adhesive-containing assemblies.

The present invention also finds significant utility in connection with more general application to the handling of stacked adhesive units. Reference is made, for example, to FIG. 11 which shows two of a potential multiplicity of adhesive units, each of which comprises an adhesive-containing patch or strip 162, which is made up of a backing layer 172 upon which is deposited an adhesive layer 170. Onto the adhesive surface of each of these layers is then applied a release layer 164. Each of these release layers 164 thus includes a single sheet of material, a laminate of material, or multiple sections 166, 168, which can be separated by one or more slits 180. When these units are in a stacked configuration, such as during their manufacture, the lower surface 167 of each of the release layers 164 is in contact with the upper surface of the adhesive layer 170 on each of the adhesive-coated layers 162. The upper surface of each of these release layers 164, however, in accordance with the present invention, also includes release coatings on both portions 166 and 168 thereof. This layer will be in contact with the backing layer 172 on the adhesive-containing patch, but any of the adhesive 170 which passes around the edge of the unit and comes in contact with the upper surfaces 166 and 168 of the release layer 164 will not now adhere to that surface, which would interrupt the manufacturing process if it were permitted to occur. In this manner, it is possible to prevent any undue sticking of the individual units to any surface of the release liner. In addition, by carefully selecting the degree of release on the upper and lower surfaces 167 and 166, 168, of release layers 164, it can be clearly controlled as to how the units separate from each other, how much force is required, etc.

Another example of the utility of the present invention can be illustrated by considering the intermediate transdermal system manufacturing step of die cutting prior to packaging. When it is desirable to die cut individual systems, but one wishes to package those systems in a separate operation, the die cut systems may be rewound on the continuous release liner after removing the waste adhesive layer. When there is a tendency for the adhesive to contact the back of the continuous release liner of the adjacent leaf in a roll, the systems may be distorted or damaged when the roll is unwound during subsequent processing steps. A release layer as described with releasing agent on both sides will prevent adjacent leaves of the roll from adhering to one another.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An assembly for adhesive attachment to the skin or mucosa of a host, said assembly comprising and innermost surface adapted to be proximate to said skin or mucosa and an outermost surface intended to be distal from said skin or mucosa, an outer backing layer corresponding to said outermost surface including an inner surface and an outer surface, a first layer of adhesive disposed on said inner surface of said outer backing layer, an inner backing layer including an inner surface and an outer surface, a second layer of adhesive disposed on said inner surface of said inner backing layer for adhesive attachment of said assembly to said skin or mucosa of said host, an intermediate release liner disposed between said first layer of adhesive and said outer surface of said inner backing layer, said intermediate release liner including an inner surface and an outer surface, both said inner surface and said outer surface of said intermediate release liner including a releasable surface, said intermediate release liner further including at least one centrally located open area, and wherein said first adhesive layer includes a portion adhesively bonded to and in direct contact with said outer surface of said inner backing layer at said at least one open area and a remaining portion of said first adhesive layer temporarily covered by said intermediate release liner, and an inner release liner covering said second layer of adhesive and comprising said innermost surface of said assembly, whereby both said intermediate release liner and said inner release liner can be adhesively released from said contact with said first layer of adhesive and said second layer of adhesive in said assembly, prior to such release can inhibit migration of components of said first and second adhesive layers, and upon removal of said inner release liner said second layer of adhesive comprises said innermost surface of said assembly for attachment to said skin or mucosa of said host.

2. The assembly of claim 1 wherein said intermediate release liner comprises a single sheet having said releasable surfaces disposed on both sides of said single sheet.

3. The assembly of claim 1 wherein said intermediate release liner comprises a laminate including at least a pair of sheets affixed to each other, each of said pair of sheets including an inner surface and an outer surface, said inner surfaces of said pair of sheets being juxtaposed with each other and each of said outer surfaces of said pair of sheets including said releasable surface.

4. The assembly of claim 3 wherein at least one of said pair of sheets comprises a transparent sheet.

5. The assembly of claim 4 wherein the other of said pair of sheets comprises an opaque sheet.

6. The assembly of claim 5 including printed material on the inner surface of the other of said pair of sheets.

7. The assembly of claim 1 wherein said intermediate release liner comprises an active agent impermeable material.

8. The assembly of claim 7 wherein said intermediate release liner is releasably adhered to both said first layer of adhesive and said inner backing layer.

9. The assembly of claim 1 wherein said first adhesive layer comprises pressure-sensitive adhesive material for adhering said assembly to the skin or mucosa of said host.

10. A system for the handling of a plurality of adhesive-coated elements, said system comprising a first adhesive-coated element including an outer backing layer having an inner surface and an outer surface, and a first layer of adhesive disposed on said inner surface of said outer backing layer, a second adhesive-coated element including an inner surface and an outer surface, said outer surface of said second adhesive-coated element including an inner backing layer and a second layer of adhesive disposed on said inner surface of said second adhesive element, an intermediate release liner disposed between and in direct contact with said first layer of adhesive and said inner backing layer of said second adhesive-coated element, and an inner release liner covering said inner surface of said second adhesive coated element, said intermediate release liner including an inner surface and an outer surface, both said inner surface and said outer surface of said intermediate release liner including a releasable surface, whereby both said intermediate release liner and said inner release liner can be adhesively released from said system and can inhibit migration of components of said first and second layers of adhesive.

11. The system of claim 10 wherein said intermediate release liner comprises a single sheet having said releasable surface disposed on both sides of said single sheet.

12. The system of claim 10 wherein said intermediate release liner comprises a laminate including at least a pair of sheets affixed to each other, each of said pair of sheets including an inner surface and an outer surface, said inner surfaces of said pair of sheets being juxtaposed with each other, and each of said outer surfaces of said pair of sheets including said releasable surface.

13. The system of claim 10 wherein at least one of said first and second adhesive-coated elements are adapted to include an active agent for release to the skin or mucosa of a host.

14. The system of claim 10 wherein said intermediate release liner comprises an active agent impermeable material.

15. The system of claim 10 wherein said intermediate release liner is releasably adhered to both said first layer of adhesive and said inner backing layer of said second adhesive-coated element.

16. The system of claim 10 wherein said first adhesive layer comprises pressure-sensitive adhesive material.

17. The system of claim 10 wherein said releasable surface on said inner surface of said intermediate release liner has a first release force, and said releasable surface on said outer surface of said intermediate release liner has a second release force, and said first and second release forces being different from each other.

18. A stacked plurality of components for the manufacture of an assembly for adhesive attachment to the skin or mucosa of a host, comprising a first plurality of outer backing layers including an inner surface and an outer surface, a plurality of first layers of adhesive disposed on said inner surfaces of said plurality of outer backing layers, and a second plurality of intermediate release liners including an inner surface and an outer surface, both said inner and outer surfaces of said second plurality of intermediate release liners including a releasable surface, whereby said first plurality of outer backing layers and said second plurality of intermediate release liners can be stacked together with said first layer of adhesive disposed on said inner surfaces of said first plurality of outer backing layers being in direct contact with said second plurality of intermediate release liners while remaining releasably attached to each other.

19. The stacked plurality of components of claim 18 wherein said intermediate release liner comprises a single sheet having said releasable surfaces disposed on both sides of said single sheet.

20. The stacked plurality of components of claim 18 wherein said second plurality of intermediate release liners comprise laminates including at least a pair of sheets affixed to each other, each of said pair of sheets including an inner surface and an outer surface, said inner surfaces of said pair of sheets being juxtaposed with each other and each of said outer surfaces of said pair of sheets including said releasable surface.

21. The stacked plurality of components of claim 20 wherein at least one of said pair of sheets comprises a transparent sheet.

22. The stacked plurality of components of claim 21 wherein the other of said pair of sheets comprises an opaque sheet.

23. The stacked plurality of components of claim 22 including printed material on the inner surface of the other of said pair of sheets.

24. The stacked plurality of components of claim 18 wherein said plurality of first layers of adhesive comprises pressure-sensitive adhesive material for adhering said assembly to the skin or mucosa of said host.

* * * * *